United States Patent
Christensen et al.

(10) Patent No.: US 8,471,060 B2
(45) Date of Patent: Jun. 25, 2013

(54) PROCESS AND REACTOR FOR THE THERMONEUTRAL CONVERSION OF ETHANOL TO ACETIC ACID

(75) Inventors: Claus Hviid Christensen, Lynge (DK); Niels Christian Schiødt, Brønshøj (DK); Bodil Voss, Virum (DK)

(73) Assignee: Haldor Topsoe A/S, Lyngby (DK)

( * ) Notice: Subject to any disclaimer, the term of this patent is extended or adjusted under 35 U.S.C. 154(b) by 377 days.

(21) Appl. No.: 12/624,019

(22) Filed: Nov. 23, 2009

(65) Prior Publication Data

US 2010/0130776 A1 May 27, 2010

(30) Foreign Application Priority Data

Nov. 27, 2008 (DK) ................................ 2008 01672

(51) Int. Cl.
*C07C 51/00* (2006.01)
(52) U.S. Cl.
USPC ........................................ 562/538
(58) Field of Classification Search
USPC ........................................ 562/538
See application file for complete search history.

(56) References Cited

U.S. PATENT DOCUMENTS

| | | | |
|---|---|---|---|
| 1,911,315 A | 5/1933 | Haner et al. | |
| 1,965,769 A | 12/1934 | Dreyfus | |
| 2,287,803 A * | 6/1942 | Hull | 562/531 |
| 2,634,295 A * | 4/1953 | MacLean | 568/406 |
| 3,248,453 A | 4/1966 | Beyrard | |
| 4,220,803 A | 9/1980 | Marcinkowsky et al. | |
| 5,840,971 A | 11/1998 | Gubelmann-Bonneau | |

FOREIGN PATENT DOCUMENTS

| | | |
|---|---|---|
| GB | 287064 A | 5/1929 |
| JP | 57102835 A | 6/1982 |

OTHER PUBLICATIONS

Inui, Kanichiro, et al. "Effective Formation of Ethyl Acetate from Ethanol over Cu-Zn-Zr-Al-O Catalyst," *Journal of Molecular Catalysis A: Chemical*, vol. 216, p. 147-156, (2004).

* cited by examiner

*Primary Examiner* — Taylor Victor Oh
(74) *Attorney, Agent, or Firm* — Dickstein Shapiro LLP

(57) ABSTRACT

A process and reactor for the production of acetic acid comprising the steps of: passing a feed stream containing ethanol and water together with a predetermined feed rate of an oxygen containing atmosphere in presence of one or more catalysts being active in simultaneous non-oxidative and oxidative conversion of ethanol to a product stream with acetic acid; recovering from the product stream a stream of acetic acid; optionally recovering reactive derivatives of acetic acid and recycling these to step (a).

4 Claims, No Drawings

PROCESS AND REACTOR FOR THE THERMONEUTRAL CONVERSION OF ETHANOL TO ACETIC ACID

BACKGROUND OF THE INVENTION

1. Field of the Invention

The present invention relates to a process for the conversion of ethanol and water to a product rich in acetic acid. More particularly, the invention is a process for combined oxidative and non-oxidative dehydrogenation of ethanol to acetic acid.

2. Description of the Related Art

Different methods for the preparation of acetic acid from ethanol have been known for many years.

Ethanol can be produced from ethylene by hydrolysis, and it may be produced by fermentation of sugars. Typically, hydrolysis of ethylene to ethanol has been preferred primarily to meet the technical use of ethanol, while fermentation of sugar containing matter is an ancient process the product of which is primarily used for household purposes. In the latter process the ethanol produced is obtained in an aqueous solution in a concentration of 5-15% by weight along with fermentation by products and solids, the so-called broth.

Typically, the ethanol is then distilled in two columns to obtain 96% ethanol and may finally be dried in a bed of zeolites to obtain anhydrous ethanol useful as an additive to gasoline.

As part of a new fuel supply development the capacity of bio-ethanol production for the use as gasoline additive has increased tremendously over the past 10 years, especially in Brazil and the US.

Ethanol can be converted by dehydrogenation to acetic acid via the oxidative and the non-oxidative route, viz.:

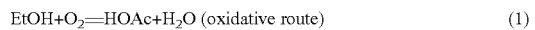
$$EtOH + O_2 = HOAc + H_2O \text{ (oxidative route)} \quad (1)$$

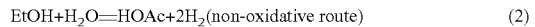
$$EtOH + H_2O = HOAc + 2H_2 \text{ (non-oxidative route)} \quad (2)$$

The oxidative route is exothermic ($-\Delta H^i = 439$ kJ/mol) and not limited by equilibrium and the non-oxidative route is endothermic ($-\Delta H^i = -44$ kJ/mol) and equilibrium limited producing acetaldehyde as an intermediate.

It is known that e.g. copper is an active catalyst for the non-oxidative dehydrogenation of ethanol to acetic acid. Other catalysts like coal are capable to convert ethanol in the non-oxidative route to acetic acid.

Some of the catalysts active in the non-oxidative route are active also in the esterification of ethanol and acetic acid, whereby ethyl acetate constitutes part of the product composition. Typical by-products in the non-oxidative route are coupling reaction products ketone, aldehyde and alcohol products, e.g. propanon, butanal and butanol.

Examples of catalysts active in the oxidative conversion of ethanol to acetic acid are vanadium oxide, gold nanoparticles and supported palladium.

Suggestions of processes to make acetic acid from ethanol are sparse.

GB 287064 discloses an acetic acid process, where an alcohol such as ethyl alcohol is passed upward in a reactor column containing in a first bed an Ag doped Cu catalyst in its reduced state and in its oxidised state at the top of the reactor. The reduced catalyst provides for dehydrogenation of ethanol to acetaldehyde, which is oxidized by contact with Cu oxide to acetic acid being withdrawn from the top of the reactor. Cu oxide is thereby reduced to copper. The Cu catalyst recovered from the bottom of the reactor may be reoxidized and recycled to the top of the reactor. This process employs a moving bed with Cu/CuO as catalyst and an oxygen carrier for the oxidation of ethanol to acetic acid via acetaldehyde.

Kanichiro Inui et al ('Effective formation of ethyl acetate from ethanol over Cu—Zn—Zr—Al—O catalyst', Journal of Molecular Catalysis A: Chemical 216 (2004), page 147-156) describes Cu—Zn—Zr—Al—O as catalysts being active in the conversion of ethanol to ethyl acetate and to acetic acid in presence of water by non-oxidative route. It is mentioned that the selectivity to propanone decreases with increasing selectivity to acetic acid. Up to 15 wt % water in the feed is described, which corresponds to 31% on a mole basis. It is proposed that the reaction proceeds via acetaldehyde, hemiacetal and ethyl acetate to acetic acid through a final hydration.

JP 57102835 discloses a non-oxidative process for the production of acetic acid from ethanol in a first ethanol dehydrogenation reaction over a CuO and other oxidic catalysts and a hydrogen separation step. In a subsequent step acetic acid together with water is separated and acetaldehyde is separated from unconverted ethanol. This process may further comprise a second acetaldehyde dehydrogenation step to acetic acid with addition of additional water, wherein the product of this step is recycled to the hydrogen separation step and unconverted ethanol is recycled to the first ethanol dehydrogenation step.

When carrying out a non-oxidative synthesis of acetic acid from ethanol, the catalyst may be arranged in an adiabatic reactor or in a heated reactor. The adiabatic reactor type is cheap to operate, however, a large temperature decrease over the reactor results in a lower product yield or requires high internal cooling rate or recycle rate in order to limit the temperature decrease over the reactor.

The heated reactor is an expensive alternative due to its more complicated construction. Furthermore, a heat source is required to supply the heat for the reaction.

The conversion of ethanol to acetic acid via the oxidative route is strongly exothermic. Due to the strong exothermic nature the reaction must be performed in a reactor type provided with efficient heat removal means, i.e. high areas of heat transfer are mandatory, which results in an expensive design. Furthermore, risks of temperature runaway and general selectivity problems are negative results of strong exothermic reactions.

In contrast to the above discussed reaction types, a process without a heat requirement, a so called thermoneutral process, does not require special means of heat supply or heat removal in the reactor. Ideally, if a chemical process takes place at a temperature higher than ambient, a slightly exothermic process supplies heat for the preheating of the feed by heat exchange with the hot reactor effluent having a temperature higher than the feed. Processes where the adiabatic temperature increase is moderate or low are considered to be thermoneutral. In context with the invention, reactions having a $\Delta H^i$ and specific heat capacity of the reactants resulting in an adiabatic change of the temperature between about −25 to 25° C. are considered thermoneutral.

SUMMARY OF THE INVENTION

The general object of this invention is to provide a process for the production of acetic acid, wherein a feed stream of ethanol and water is converted to acetic acid in a thermoneutral manner.

It has been found that a feed stream comprising ethanol, water and oxygen can be converted over a bed of reduced copper based catalyst at thermoneutral conditions with a high yield of acetic acid and considerably reduced formation of carbon dioxide compared to the oxidative acetic acid reaction. The condition of such a process require adjustment of the oxygen content in the feed in such manner as to allow for a thermoneutral process without suffering a severe loss of selectivity.

Pursuant to the above findings, the present invention is a process for the production of acetic acid comprising the steps of:

(a) passing a feed stream containing ethanol and water together with a predetermined feed rate of an oxygen containing atmosphere in presence of one or more catalysts being active in simultaneous non-oxidative and oxidative conversion of ethanol to a product stream with acetic acid according to the following reaction:

$$CH_3CH_2OH + yH_2O + xO_2 = CH_3COOH + 2(1-x)H_2 + y - (1-2x)H_2O,$$

wherein
x is the molar ratio of oxygen to ethanol,
y is the molar ratio of water to ethanol, and
wherein
y is at least (1−2x);

(b) recovering from the product stream a stream of acetic acid;
(c) optionally recovering reactive derivatives of acetic acid and recycling these to step (a).

Typical operation temperatures for the catalytic conversion of ethanol to acetic acid are 250-450° C., preferably about 250-350° C. The operation pressure is between 0 and 10 bar, preferably 0-3 bar.

A thermoneutral process in accordance with the previous definition is controlled by the molar ratio of oxygen to ethanol.

The amount of the oxygen containing atmosphere is preferably adjusted so that the exit temperature from the reaction is higher than the inlet temperature in order to supply heat for preheating of the feed stream with the hot product stream.

The dehydrogenation reactions of ethanol to acetic acid proceed by the following reaction schemes:

$$CH_3CH_2OH + H_2O = CH_3COOH + 2H_2 \quad \text{(endothermic, non-oxidative)}$$

$$2xH_2 + xO_2 = 2xH_2O \quad \text{(exothermic oxidation of hydrogen)}$$

where x is the fraction of ethanol converted by the oxidative reaction (1)

A balance of the standard heats of reaction requires a stoichiometry representing 91% non-oxidative and 9% oxidative, i.e. x=0.09, or $CH_3CH_2OH + 0.82H_2O + 0.09 O_2 = CH_3COOH + 1.82H_2$.

In a thermoneutral process being within the scope of the invention, x may deviate from 0.09 and still provide for a temperature increase/decrease of less than 25° C. Preferably, the molar ratio of oxygen to ethanol is between 0.0045 and 0.25.

The by-product formation of $CO_2$ proceeds according to the reaction scheme:

$$CH_3CH_2OH + 3O_2 = 2CO_2 + 3H_2O$$

The utility of the process depends on the selectivity towards acetic acid instead of carbon dioxide in the oxidative conversion part of ethanol to acetic acid.

A stoichiometric ratio of ethanol to water in a thermoneutral process for the conversion of ethanol and water to acetic acid can be adjusted in e.g. a side stream from an ethanol plant producing bio-ethanol or fuel-ethanol, thereby de-bottlenecking the ethanol production. Such a side-stream may advantageously be obtained as a vapour stream withdrawn from the distillation section of the ethanol plant, whereby a need for evaporation of the ethanol/water feed is avoided. The amount of oxygen to be added for obtaining a thermoneutral process is moderate and appropriate ratios may be obtained by adding compressed atmospheric air to the process.

It may therefore be advantageous to integrate the process according to the invention into an ethanol plant, where ethanol and water are present in suitable concentrations and especially where the feed is vaporised.

The hydrogen co-product generated during the process may be recovered from the product mixture in a hydrogen rich stream by conventional methods such as phase separation, distillation, membrane etc.

The recovered hydrogen rich stream can be passed to a fuel cell in order to convert chemical energy to electrical power and heat. Advantageously, the fuel cell is of a type where the heat generated is removed at a temperature which can supply the heat needed in the ethanol plant or the acetic acid plant, e.g. for distillation reboiler or preheating. Another advantage of combining the acetic acid plant with a fuel cell is that the air supply is common to the dehydrogenation process as well as to the fuel cell.

In both processes the air is preferably supplied at a pressure slightly above atmospheric pressure, e.g. 1-5 bar. By employing the air blower for the supply of air to both units, a reduction of the inventory is achieved. Thus, in a preferred embodiment of the invention the hydrogen rich product from the dehydrogenation process is passed to a fuel cell for the generation of electricity and heat, the fuel cell being supplied with air for the oxidation of the fuel from an air blower supplies additionally air to the acetic acid process.

Catalyst/s being useful in the process according to the invention are any being active in the conversion of ethanol to acetic acid via the oxidative and non-oxidative route. The group of useful catalysts include those which further catalyse the conversion of ethanol with acetic acid to obtain ethyl acetate. Examples of catalysts active in the dehydrogenation of ethanol with water to acetic acid are Cu based, optionally in combination with zinc oxide, chromium oxide, manganese oxide, zirconium oxide and/or aluminium oxide, or a catalyst comprising the above supported on an inert carrier.

The invention provides furthermore a reactor for the thermoneutral production of acetic acid as described hereinbefore.

The reactor according to invention comprises a first and at least a second fixed catalyst bed with one or more catalysts being active in simultaneous non-oxidative and oxidative conversion of ethanol to acetic acid;

inlet means for a feed stream comprising ethanol, water and a first portion of an oxygen containing atmosphere to the first catalyst bed;

between the first and at least second catalyst bed inlet means for a second portion of the oxygen containing atmosphere and means for distributing and mixing the second portion of the oxygen containing atmosphere into an effluent of partly converted feed stream from the first catalyst bed; and means for passing the partly converted feed stream and admixed with the oxygen containing atmosphere into the at least second catalyst bed.

DETAILED DESCRIPTION OF THE PREFERRED EMBODIMENTS

The above invention will be described in more detail in the below Examples 1 and 2.

In Example 1, a product stream rich in acetic acid is prepared by passage of a feed composition having a stoichiometry corresponding to a thermoneutral dehydrogenation of ethanol to acetic acid over a bed of catalyst being active both in the oxidative and the non-oxidative dehydrogenation of ethanol and water for the preparation of the acetic acid product.

Example 1

In an experimental setup a feed stream of 52.7% ethanol, 47.3% water was fed at a rate of 21.4 g/h by a HPLC pump. The feed stream was evaporated, mixed with $O_2$ at a rate of 0.77 Nl/h and passed over a $CuAl_2O_4$ catalyst at 320° C. and atmospheric pressure in gas phase together with a nitrogen carrier gas stream at a feed rate of 11.5 Nl/h. The product obtained from the conversion was fractioned into a condensate and a gas fraction. The produced condensate was formed at rate of 16.9 g/h and had a composition of 55.95% $H_2O$, 14.66% acetic acid, 20.12% acetaldehyde, 8.39% ethanol, 0.62% ethyl acetate and less than 0.3% coupling byproducts. The gas fraction was formed at a rate of 21.2 Nl/h having a composition of 54.19% $N_2$, 0.73% $CO_2$, 11.11% acetaldehyde and 33.96% hydrogen.

As can be calculated from above figures the selectivity of ethanol to acetic acid or reactive derivatives is 98.8%.

Example 2

The experiment in Example 1 was repeated; however, oxygen was added in two portions. In an experimental setup a feed stream of 52.7% ethanol, 47.3% water was fed at a rate of 21.4 g/h by a HPLC pump, mixed with $O_2$ at a rate of 0.385 Nl/h and passed over 5 g of the catalyst at 320° C. and atmospheric pressure in the gas phase together with a nitrogen carrier gas stream at a feed rate of 11.4 Nl/h. The product obtained from the first conversion was mixed with further a second portion of $O_2$ at a rate of 0.385 Nl/h and passed over second bed of the catalyst maintained at 320° C. The product obtained from the second conversion was cooled and fractioned into a condensate and a gas fraction. A condensate rate of 17.1 g/h with a composition of 56.33% $H_2O$, 14.55% acetic acid, 19.98% acetaldehyde, 8.27% ethanol 0.61% ethyl acetate and less than 0.3% coupling byproducts was obtained. A product gas rate of 20.9 Nl/h was measured with a composition of 55.1% N2, 0.25% $CO_2$, 11.4% acetaldehyde and 33.3% hydrogen.

As can be calculated from above figures the selectivity of ethanol to carbon dioxide of 0.46 is found, which is only one third of the selectivity found with one addition of oxygen.

What is claimed is:

1. Process for the production of acetic acid comprising the steps of:
    (a) passing a feed stream containing ethanol and water together with a predetermined feed rate of an oxygen containing atmosphere in presence of one or more catalysts being active in simultaneous non-oxidative and oxidative conversion of ethanol to a product stream with acetic acid at a temperature between 250-450° C. and in vapor phase according to the following reaction:

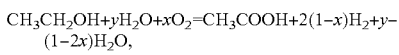

$$CH_3CH_2OH + yH_2O + xO_2 = CH_3COOH + 2(1-x)H_2 + y - (1-2x)H_2O,$$

wherein
    x is the molar ratio of oxygen to ethanol,
    y is the molar ratio of water to ethanol and wherein
    y is at least (1−2x); and
    (b) recovering from the product stream a stream of acetic acid;
    wherein the feed rate of the oxygen containing atmosphere corresponds to a molar ratio of oxygen to ethanol is between 0.0045 and 0.25, and wherein the molar ratio of water to ethanol is at least 0.5.

2. Process of claim 1, wherein the oxygen containing atmosphere is air.

3. Process in accordance with claim 1, wherein the feed stream of water and ethanol is a side-stream from an ethanol-plant.

4. Process of claim 3, wherein the side-stream is withdrawn from a distillation section of the ethanol plant.

* * * * *